US009333316B2

(12) United States Patent
Kiani

(10) Patent No.: US 9,333,316 B2
(45) Date of Patent: *May 10, 2016

(54) DRUG ADMINISTRATION CONTROLLER

(75) Inventor: Massi E. Kiani, Laguna Niguel, CA (US)

(73) Assignee: MASIMO CORPORATION, Irvine, CA (US)

( * ) Notice: Subject to any disclaimer, the term of this patent is extended or adjusted under 35 U.S.C. 154(b) by 657 days.

This patent is subject to a terminal disclaimer.

(21) Appl. No.: 13/475,136

(22) Filed: May 18, 2012

(65) Prior Publication Data

US 2012/0227739 A1    Sep. 13, 2012

Related U.S. Application Data

(63) Continuation of application No. 11/654,904, filed on Jan. 17, 2007, now Pat. No. 8,182,443.

(60) Provisional application No. 60/759,673, filed on Jan. 17, 2006, provisional application No. 60/764,946, filed on Feb. 2, 2006.

(51) Int. Cl.
  *A61M 31/00* (2006.01)
  *A61M 16/12* (2006.01)
  *A61M 5/172* (2006.01)

(52) U.S. Cl.
  CPC .............. *A61M 16/12* (2013.01); *A61M 5/1723* (2013.01); *A61M 2202/0233* (2013.01); *A61M 2205/18* (2013.01); *A61M 2205/3313* (2013.01); *A61M 2205/3375* (2013.01); *A61M 2205/3561* (2013.01); *A61M 2205/3592* (2013.01); *A61M 2205/502* (2013.01); *A61M 2230/005* (2013.01); *A61M 2230/04* (2013.01); *A61M 2230/10* (2013.01); *A61M 2230/205* (2013.01); *A61M 2230/207* (2013.01); *A61M 2230/30* (2013.01); *A61M 2230/42* (2013.01); *A61M 2230/432* (2013.01); *A61M 2230/50* (2013.01)

(58) Field of Classification Search
  CPC ..................... A61M 2205/18; A61M 2205/33; A61M 2205/3303; A61M 2205/3306; A61M 2230/005; A61M 2230/207; A61M 2230/30; A61M 2230/42; A61M 5/172; A61M 5/1723; A61M 5/168; A61M 16/12; A61M 2230/10; A61M 2202/0233; A61M 2230/50; A61M 2230/205; A61M 2205/3561; A61M 2230/04; A61M 2205/3313; A61M 2205/3375; A61M 2205/3592; A61M 2205/502
  USPC ......... 604/28, 31, 65–67, 131, 500, 503, 504; 600/301; 128/903, 204.23
  See application file for complete search history.

(56) References Cited

U.S. PATENT DOCUMENTS

| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |

(Continued)

*Primary Examiner* — Bhisma Mehta
*Assistant Examiner* — Bradley G Thomas, Jr.
(74) *Attorney, Agent, or Firm* — Knobbe, Martens, Olson & Bear LLP

(57) ABSTRACT

A drug administration controller has a sensor that generates a sensor signal to a physiological measurement device, which measures a physiological parameter in response. A control output responsive to the physiological parameter or a metric derived from the physiological parameter causes a drug administration device to affect the treatment of a person, such as by initiating, pausing, halting or adjusting the dosage of drugs administered to the person.

7 Claims, 9 Drawing Sheets

(56) References Cited

U.S. PATENT DOCUMENTS

| | | |
|---|---|---|
| 5,163,438 A | 11/1992 | Gordon et al. |
| 5,305,745 A * | 4/1994 | Zacouto ............ 600/324 |
| 5,337,744 A | 8/1994 | Branigan |
| D353,195 S | 12/1994 | Savage et al. |
| D353,196 S | 12/1994 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A * | 6/1997 | Kiani-Azarbayjany et al. ............ 600/316 |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,957,885 A * | 9/1999 | Bollish et al. ............ 604/67 |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,933 B2 | 7/2003 | Kiani et al. |
| 6,606,511 B1 | 8/2003 | Ali et al. |
| 6,622,095 B2 * | 9/2003 | Kobayashi et al. ............ 702/31 |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,585 B1 | 4/2004 | Parker |
| 6,725,075 B2 | 4/2004 | Al-Ali |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Al et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |

(56) References Cited

U.S. PATENT DOCUMENTS

| | | |
|---|---|---|
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 2004/0092805 A1* | 5/2004 | Yarita .......................... 600/310 |

* cited by examiner

DRUG ADMINISTRATION CONTROLLER

CROSS-REFERENCE TO RELATED APPLICATIONS

The present application is a continuation of U.S. patent application Ser. No. 11/654,904, filed Jan. 17, 2007, entitled Drug Administration Controller, which claims priority benefit under 35 U.S.C. §119(e) to U.S. Provisional Patent Application Ser. No. 60/759,673, filed Jan. 17, 2006, entitled Drug Administration Controller, and Ser. No. 60/764,946, filed Feb. 2, 2006, entitled Drug Administration Controller, all of which are incorporated by reference herein in their entireties.

BACKGROUND

Physiological measurement systems employed in healthcare often feature visual and audible alarm mechanisms that alert a caregiver when a patient's vital signs are outside of predetermined limits. For example, a pulse oximeter, which measures the oxygen saturation level of arterial blood, indicates oxygen supply. A typical pulse oximetry system has a sensor that provides a signal output to a pulse oximeter monitor. The sensor has an emitter configured with both red and infrared LEDs that project light through a fleshy medium to a detector so as to determine the ratio of oxygenated and deoxygenated hemoglobin light absorption. The monitor has a signal processor, a display and an alarm. The signal processor inputs the conditioned and digitized sensor signal and calculates oxygen saturation ($SpO_2$) along with pulse rate (PR), as is well-known in the art. The display provides a numerical readout of a patient's oxygen saturation and pulse rate. The alarm provides an audible indication when oxygen saturation or pulse rate are outside of predetermined limits.

Another pulse oximetry parameter is perfusion index (PI). PI is a measure of perfusion at the pulse oximetry sensor site comparing the pulsatile (AC) signal to the non-pulsatile (DC) signal, expressed as a percentage ratio. An example is the PI Delta Alarm™ feature of the Radical 7™ Pulse CO-Oximeter™ available from Masimo Corporation, Irvine, Calif., which alerts clinicians to specified changes in PI. In particular, PI Delta indicates if PI at a monitored site decreases by a specific level (delta) over a specified window of time, with both variables selectable by the user within predetermined ranges.

Tracking a series of desaturations over time is one metric that is derived from $SpO_2$ that is well-known in the art. See, e.g., Farney, Robert J., Jensen, Robert L.; *Ear Oximetry to Detect Apnea and Differentiate Rapid Eye Movement (REM) and Non-REM (NREM) Sleep: Screening for the Sleep Apnea Syndrome*; Chest; April 1986; pages 533-539, incorporated by reference herein. Traditional high and low $SpO_2$ alarm limits alert clinicians to saturation levels that exceed user selected thresholds, and these thresholds are typically established at a considerable change from the patients' baseline saturation level. However, in select patient populations, substantial desaturation events that exceed a typical low alarm limit threshold may be preceded by a cycle of transient desaturations over a limited timeframe. The ability to alert clinicians to a cycle of these smaller desaturations provides an earlier indication of a potential significant decline in the patient's status and the need for more focused monitoring and/or a change in treatment. An example is the Desat Index Alarm™ feature of the Radical 7™, mentioned above, which enables clinicians to detect an increasing quantity of smaller desaturations that may precede declining respiratory status. Desat Index is a measure responsive to patients that experience a specific number of desaturations beyond a defined level from the patient's baseline saturation over a specific window of time, with each of these variables selectable by the user within predetermined ranges.

A physiological parameter that can be measured in addition to, or in lieu of, $SpO_2$ is respiration rate (RR). A respiration rate monitor utilizes a body sound sensor with piezoelectric membranes particularly suited for the capture of acoustic waves and the conversion thereof into electric signals. To detect body sound, the piezoelectric membranes are used as mechano-electric transducers that are temporarily polarized when subject to a physical force, such as when subjected to the mechanical stress caused by the acoustic waves coming from the inside of a patient's body. The body sound sensor is typically attached to the suprasternal notch or at the lateral neck near the pharynx so as to detect tracheal sounds. A sound sensor is described in U.S. Pat. No. 6,661,161 entitled Piezoelectric Biological Sound Monitor With Printed Circuit Board, incorporated by reference herein. A respiration rate monitor is described in U.S. patent application Ser. No. 11/547,570 entitled Non-Invasive Monitoring of Respiratory Rate, Heart Rate and Apnea, incorporated by reference herein.

SUMMARY

Conventional patient monitors give insufficient advance warning of deteriorating patient health or the onset of a potentially serious physiological condition. Advantageously, a drug administration controller is responsive to one or more physiological parameters in addition to, or in lieu of, $SpO_2$ and PR, such as carboxyhemoglobin (HbCO), methemoglobin (HbMet), perfusion index (PI) and respiration rate (RR), to name a few. Further, a drug administration controller is advantageously responsive not only to preset parameter limits but also to various metrics derived from measured physiological parameters, such as trends, patterns and variability, alone or in combination, to name a few. As such, a drug administration controller is adapted to pausing or otherwise affecting drug administration based upon one or more physiological parameters and one or more metrics. Parameter variability is described with respect to PI in U.S. patent application Ser. No. 11/094,813 entitled Physiological Assessment System, incorporated by reference herein.

As an example, a drug administration controller may be responsive to changes in HbMet. Gaseous nitric oxide (NO) is increasingly recognized as an effective bacteriostatic or bacteriocidal agent. NO, however, can toxically increase HbMet.

A drug administration controller may be responsive to changes in perfusion index, such as measured by PI Delta, described above. PI may change dramatically in response to sympathetic changes in vasoconstriction or vasodilation of peripheral vessels caused by anesthesia or pain. For example, painful stimulus causes a significant decline of perfusion index.

As another example, a drug administration controller may be responsive to a cycle of transient desaturations over a limited timeframe, such as indicated by Desat Index, described above. Patients receiving pain medication may be predisposed to respiratory depression. If the patient has an underlying respiratory condition, pain medication may cause the patient to spiral into a cascade of cyclic desaturations, which initially are mild but may worsen quickly, leading to respiratory depression and even arrest.

As a further example, a drug administration controller may be responsive to respiration rate (RR) monitoring, as described above. RR provides an accurate marker for indicating acute respiratory dysfunction. For example, during conscious sedation, there is a risk of respiratory depression, and changes in RR typically provide an earlier warning than does pulse oximetry alone.

DETAILED DESCRIPTION

Figure 1:
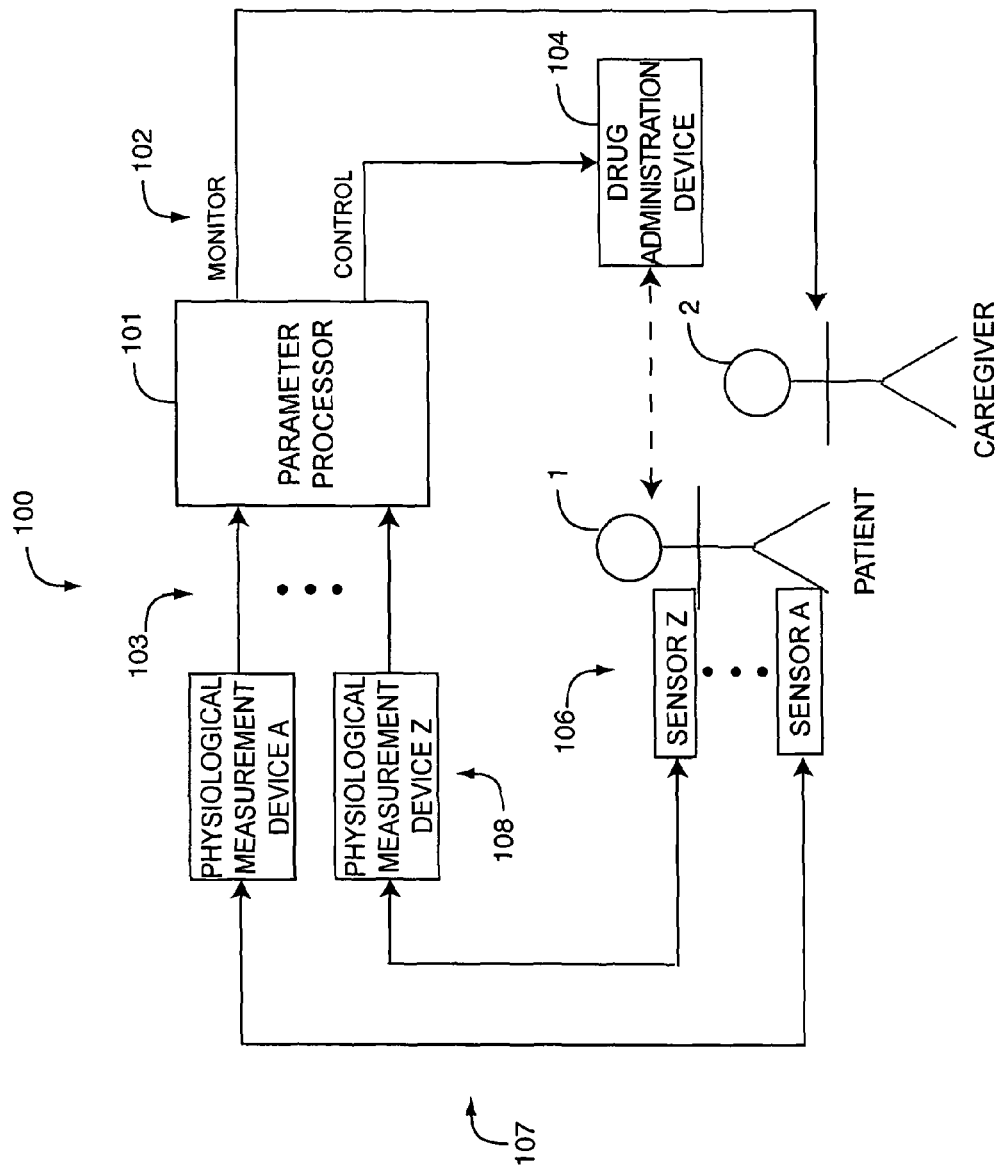
FIG. 1 is a general block diagram of a drug administration controller.

FIG. 1 illustrates a drug administration controller 100 having one or more sensors 106 generating sensor signals 107 in response to physiological states of a living being, such as a patient 1. One or more physiological measurement devices 108 generate physiological parameter measurements 103 in response to the sensor Signals 107. A multiple parameter processor 101 processes the parameter measurements 103 alone or in combination and generates monitor or control outputs 102, or both, in response. In an open-loop configuration, one or more monitor outputs 102 are observed by a caregiver 2, who administers drugs or alters drug doses in response. Alternatively, or in addition to, the caregiver 2 initiates, pauses, halts or adjusts the settings of a drug administration device 104. In a closed-loop configuration, a drug administration device 104 is responsive to one or more control outputs 102 so as to affect the treatment of the patient 1, including initiating, pausing, halting or adjusting the dosage of administered drugs.

As shown in FIG. 1, the drug administration device may be, as examples, a drug infusion device or a medical gas inhalation device. Closed loop drug infusion control is described in U.S. patent application Ser. No. 11/075,389, entitled Physiological Parameter Controller, incorporated by reference herein. Closed loop respirator control is described in U.S. Pat. App. No. 60/729,470 entitled Multi-Channel Pulse Oximetry Ventilator Control, incorporated by reference herein.

Also shown in FIG. 1, sensors 106 may include an optical sensor attached to a tissue site, such as a fingertip, for measuring one or more blood parameters. Sensors 106 may also include blood pressure cuffs, ECG or EEG electrodes, $CO_2$ measuring capnography sensors and temperature sensors to name but a few. Corresponding physiological measurement devices 108 responsive to these sensors 106 may include blood parameter monitors, blood pressure monitors, capnometers, ECG and EEG monitors, as a few examples.

In one embodiment, sensors 106 include a pulse oximetry sensor, such as described in U.S. Pat. No. 5,782,757 entitled Low Noise Optical Probes and physiological measurement devices 108 include a pulse oximeter, such as described in U.S. Pat. No. 5,632,272 entitled Signal Processing Apparatus, both assigned to Masimo Corporation, Irvine, Calif. and both incorporated by reference herein. In another embodiment, sensors 106 and measurement devices 108 include a multiple wavelength sensor and a corresponding noninvasive blood parameter monitor, such as the RAD-57™ and Radical-7™ for measuring $SpO_2$, CO, HbMet, pulse rate, perfusion index and signal quality. The RAD-57 and Radical-7 are available from Masimo Corporation, Irvine, Calif. In other embodiments, sensors 106 also include any of LNOP® adhesive or reusable sensors, SofTouch™ sensors, Hi-Fi Trauma™ or Blue™ sensor all available from Masimo Corporation, Irvine, Calif. Further, measurement devices 108 also include any of Radical®, SatShare™, Rad-9™, Rad-5™, Rad-5v™ or PPO+™ Masimo SET® pulse oximeters all available from Masimo Corporation, Irvine, Calif.

In a particular embodiment, the control or monitor outputs 102 or both are responsive to a Desat Index or a PI Delta or both, as described above. In another particular embodiment, one or more of the measurement devices 108, the parameter processor 101 and the drug administrative device 104 are incorporated within a single unit. For example, the devices may be incorporated within a single housing, or the devices may be separately housed but physically and proximately connected.

Although sensors 106 are described above with respect to noninvasive technologies, sensors 106 may be invasive or noninvasive. Invasive measurements may require a person to prepare a blood or tissue sample, which is then processed by a physiological measurement device.

Figure 2A:
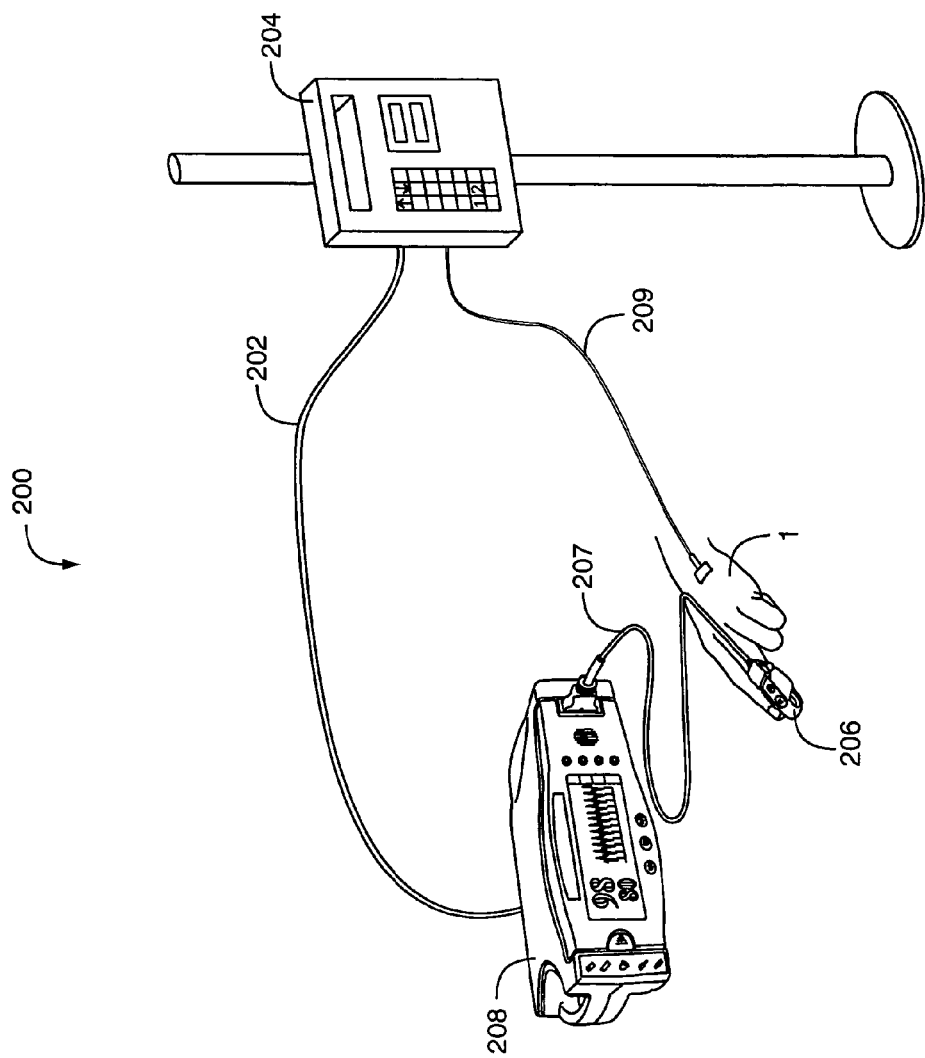
FIGS. 2A-C are illustrations of drug infusion controller embodiments.

FIG. 2A illustrates a drug infusion controller embodiment 200 comprising a drug-infusion pump 204, an optical sensor 206 attached to a patient 1 and a noninvasive blood parameter monitor 208. The optical sensor 206 provides a sensor Signal via a sensor cable 207 to the blood parameter monitor 208. The blood parameter monitor 208 generates blood parameter measurements and processes those parameters to generate monitor and control outputs 203 (FIG. 1), as described in further detail with respect to FIGS. 4-5, below. In particular, the blood parameter monitor 208 generates control signals via a control cable 202 to the drug-infusion pump 204, and the drug-infusion pump 204 administers drugs to the patient 1 via an IV 209, accordingly.

In one embodiment, the administered drug is a nitrate, such as sodium nitroprusside, and the blood parameter monitored is HbMet. In a particular embodiment, the blood parameter monitor 208 provides a control output according to one or more entries in TABLE 1. In another particular embodiment, the blood parameter monitor 208 provides a control output according to one or more entries in TABLE 2. In yet another embodiment, a blood parameter monitor 208 confirms that the measurement of HbMet is accurate, such as by checking a signal quality parameter or by having multiple sensors 206 on the patient 1.

Figure 2B:
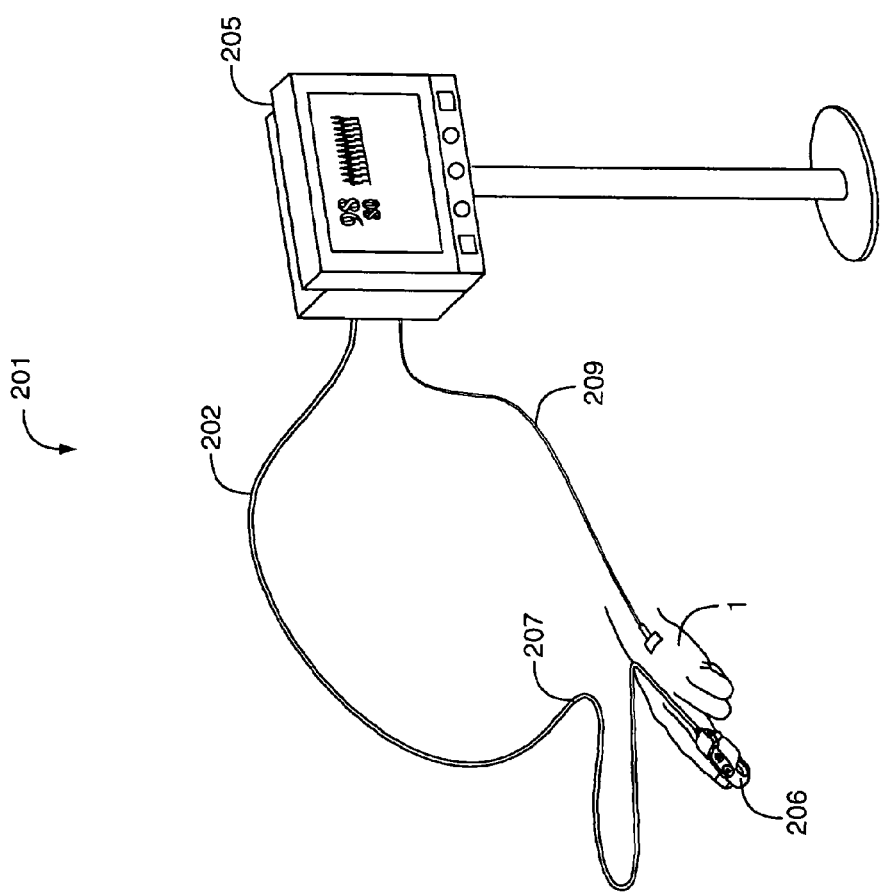

FIG. 2B illustrates another drug infusion controller embodiment 201 comprising an optical sensor 206 and a combination blood-parameter monitor/drug infusion pump 205. In an embodiment, the drug infusion controller 200, 201 provides a visual display or audible alarm indicating various degrees of patient condition, such as green, yellow and red indicators or intermittent and low volume, medium volume and high volume tones.

TABLE 1

Rule Based Monitor Outputs

| RULE | OUTPUT |
|---|---|
| If HbMet > limit threshold | disable pump; trigger alarm |
| if HbMet > trend threshold | disable pump; trigger alarm |

TABLE 2

| Rule-Based Monitor Outputs | |
|---|---|
| RULE | OUTPUT |
| If HbMet > limit threshold | disable pump; trigger alarm |
| if HbMet > trend threshold | reduce dosage; activate caution indicator |

Another embodiment involves patient controlled analgesia (PCA), i.e. the administered drug is an analgesia, and administration of the drug is controlled by the patient according to perceived pain levels. Analgesia administration, however, is paused in response to one or more blood parameters and corresponding metrics. In one embodiment, the blood parameter monitored is $SpO_2$ and the blood parameter monitor 208 provides a control output responsive to Desat Index. In a particular embodiment, PCA is paused or disabled according to TABLE 3.

TABLE 3

| Rule Based PCA Control Outputs | |
|---|---|
| RULE | OUTPUT |
| If Desat Index > index limit | pause PCA for predetermined period; activate alarm |

In another embodiment, the blood parameter monitor 208 provides a control output responsive to a PI indication of pain. In this manner, the administration of anesthesia is controlled according to the patient's perceived pain level. In a particular embodiment, PCA is paused or enabled according to one or more entries of TABLE 4, where a falling PI results in a negative PI Delta relative to an established baseline.

TABLE 4

| Rule Based PCA Control Outputs | |
|---|---|
| RULE | OUTPUT |
| If PI Delta < delta limit | enable PCA; activate caution indicator |
| If PI Delta < delta limit | disable PCA |

Figure 2C:
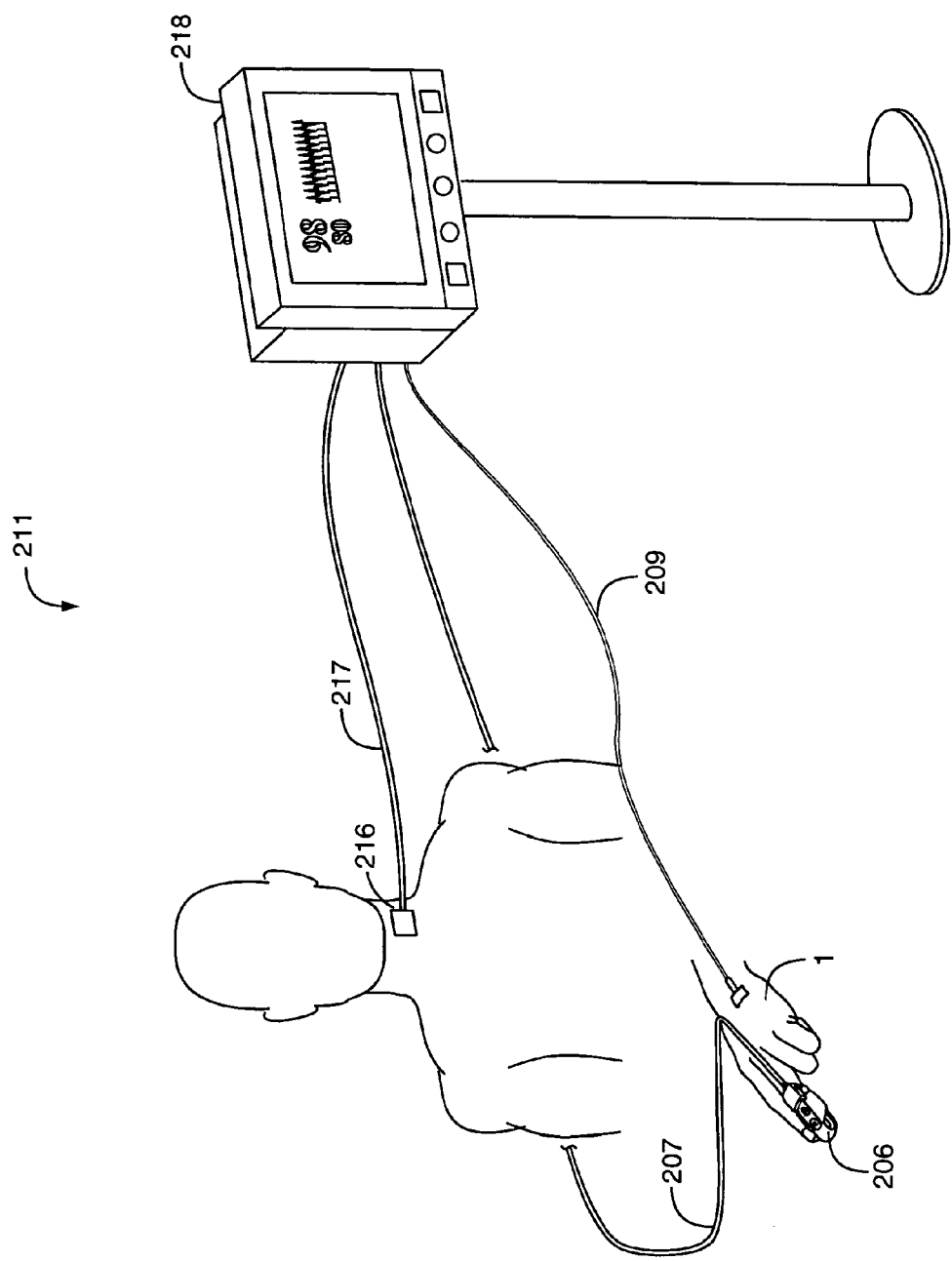

FIG. 2C illustrates yet another drug infusion controller embodiment 211 having a piezoelectric sensor 216 and a combination blood-parameter/piezoelectric sound monitor/drug infusion pump 218. A piezoelectric sensor 216 is attached to a patient's body 1 so as to detect tracheal sounds. The corresponding sensor signal is transmitted to the sound monitor 218 via a sensor cable 217. The sound monitor/pump 218 generates biological sound measurements such as respiration rate (RR) and processes the measurements to generate control outputs. In a particular embodiment, the monitor/pump 218 provides a control output according to one or more entries of TABLE 5.

TABLE 5

| Rule Based Monitor Outputs | |
|---|---|
| RULE | OUTPUT |
| If RR trend < trend threshold | reduce dosage; activate caution indicator |
| If RR < limit threshold | disable pump; trigger alarm |

Figure 3A:
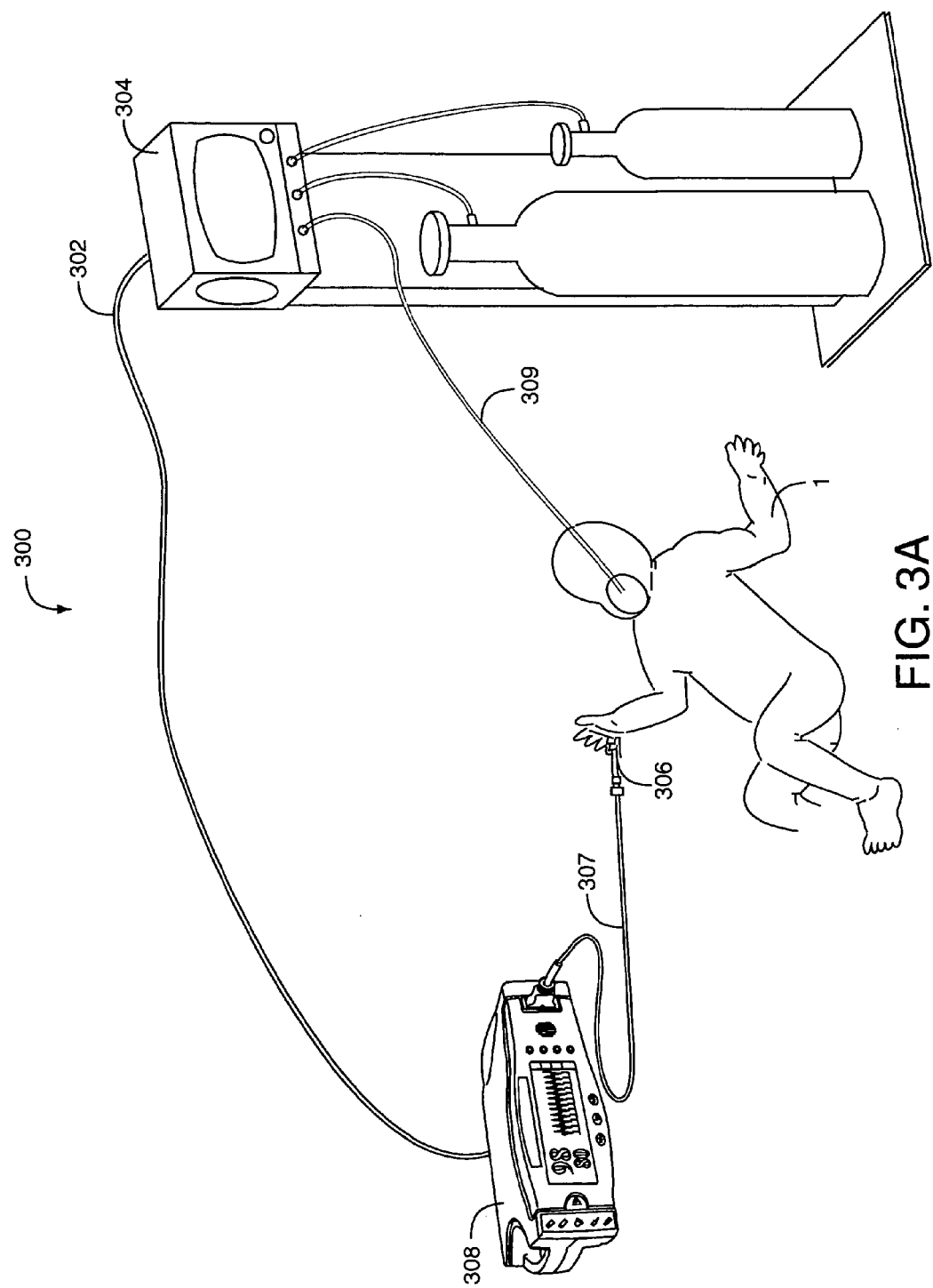
FIGS. 3A-C are illustrations of medical gas controller embodiments.
Figure 3B:
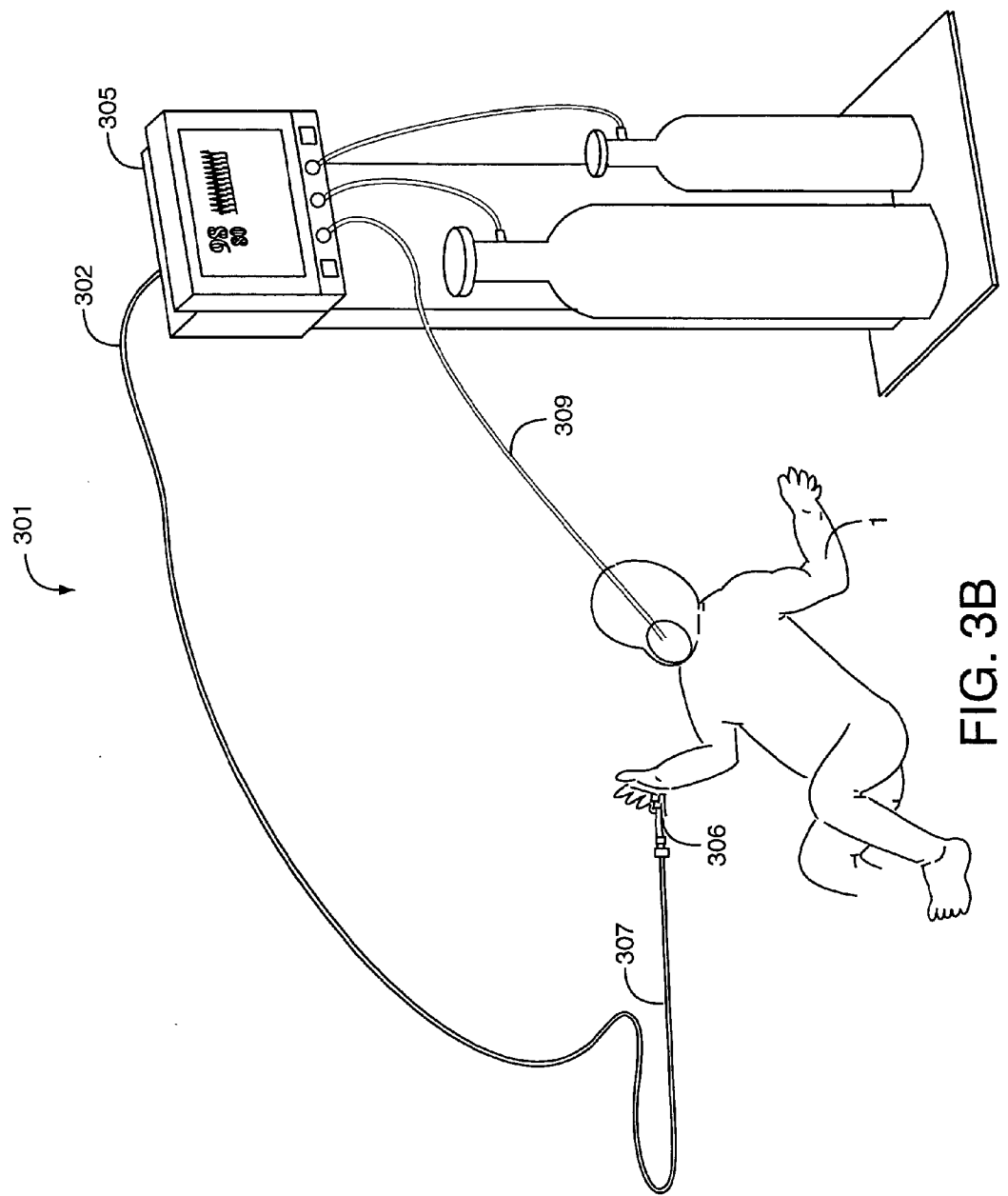

FIG. 3A illustrates a medical gas controller embodiment 300 comprising a ventilator 304 adapted to supply both oxygen and a medical gas, an optical sensor 306 attached to a patient 1, and a noninvasive blood parameter monitor 308. The optical sensor 306 provides a sensor signal via a sensor cable 307 to the blood parameter monitor 308. The blood parameter monitor 308 generates blood parameter measurements and processes those parameters to generate monitor and control outputs, as described with respect to FIGS. 4-5, below. In particular, the blood parameter monitor 308 generates control signals via a control cable 302 to the ventilator 304, and the ventilator 304 administers a medical gas to the patient 1 via a breathing apparatus 309 accordingly. FIG. 3B illustrates another medical gas controller embodiment 301 comprising an optical sensor 306 and a combination blood-parameter monitor/ventilator 305.

In one embodiment, the administered medical gas is a NO, and the blood parameter monitored is HbMet. In a particular embodiment, the blood parameter monitor 308 provides a control output according to one or more entries of TABLE 6. In another particular embodiment, the blood parameter monitor 308 provides a control output according to one or more entries of TABLE 7. In yet another embodiment, a blood parameter monitor 308 confirms that the measurement of HbMet is accurate, such as by checking a signal quality parameter or by having multiple sensors 306 on the patient 1. In a further embodiment, the administered medical gas is CO, and the blood parameter monitored is HbCO.

TABLE 6

| Rule Based Monitor Outputs | |
|---|---|
| RULE | OUTPUT |
| If HbMet trend > trend threshold | halt NO flow; trigger alarm |
| If HbMet > limit threshold | halt NO flow; trigger alarm |

TABLE 7

| Rule Based Monitor Outputs | |
|---|---|
| RULE | OUTPUT |
| If HbMet trend > trend threshold | reduce NO flow; activate caution indicator |
| If HbMet > limit threshold | halt NO flow; trigger alarm |

Figure 3C:
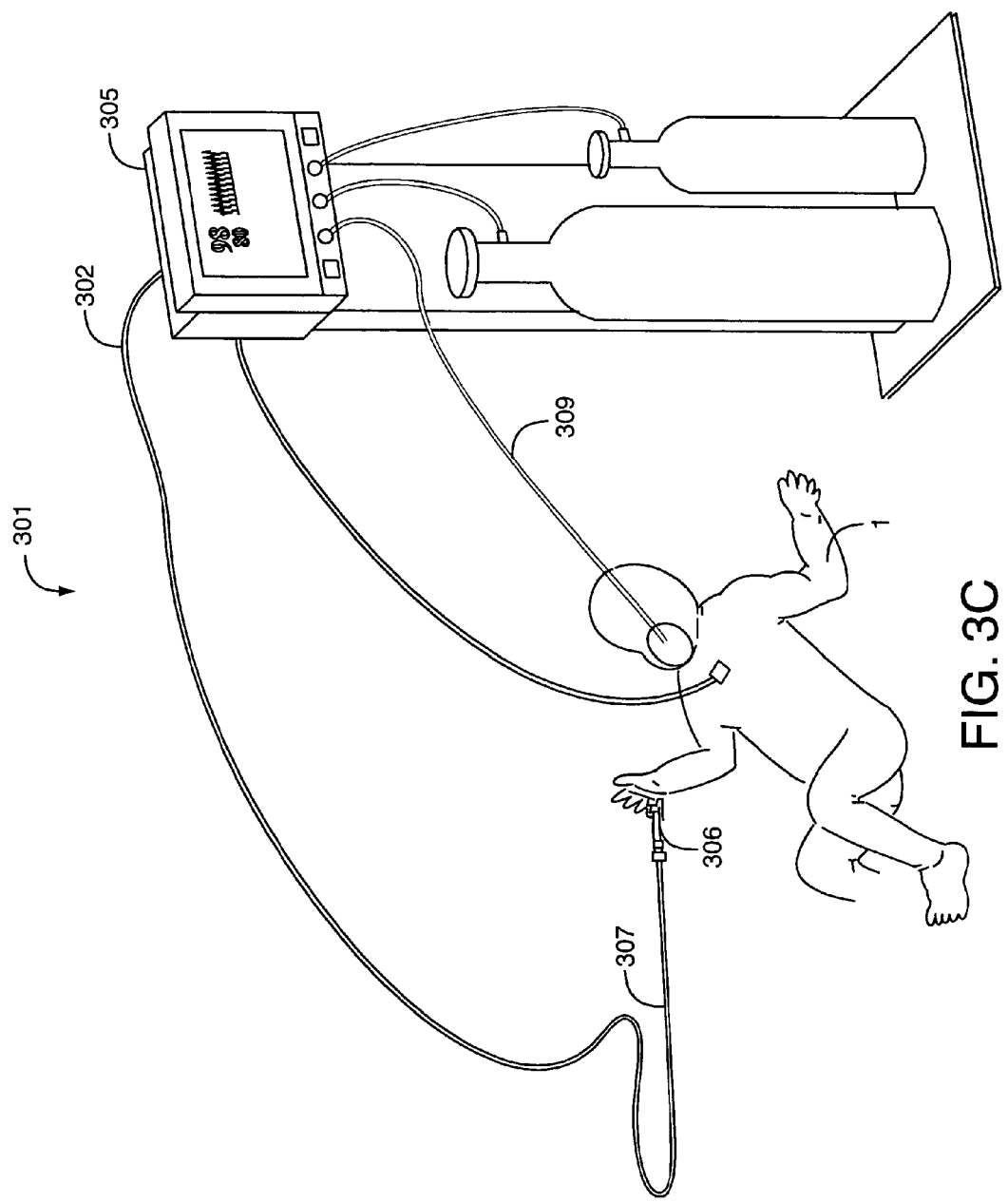

FIG. 3C illustrates yet another medical gas controller embodiment 311 comprising a piezoelectric sound sensor 316 and a combination blood parameter/piezoelectric sound monitor/ventilator 315. The sound sensor 316 is attached to a patient's body 1 so as to detect tracheal sounds and provides a sensor signal via a sensor cable 317 to the sound monitor 315. The sound monitor/ventilator 315 generates biological sound measurements such as respiration rate (RR) and provides control outputs responsive to RR. In a particular embodiment, the monitor/ventilator 315 provides a control output according to one or more entries of TABLE 8.

TABLE 8

| Rule Based Monitor Outputs | |
|---|---|
| RULE | OUTPUT |
| If RR trend < trend threshold | reduce medical gas flow; activate caution indicator |
| If RR limit < limit threshold | halt medical gas flow; trigger alarm |

Figure 4:
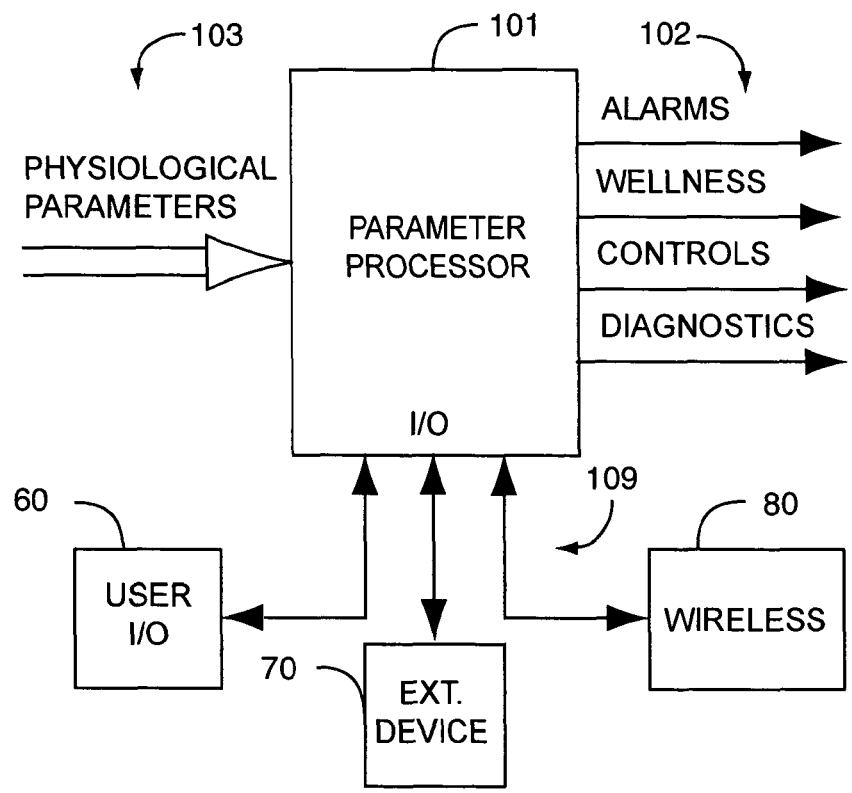
FIG. 4 is a general block diagram of a parameter processor embodiment.

FIG. 4 illustrates a parameter processor 101, which may comprise an expert system, a neural-network or a logic circuit as examples. The parameter processor 101 has as inputs 103 one or more parameters from one or more physiological measurement devices 108 (FIG. 1). Noninvasive parameters may include oxygen saturation (SpO$_2$), pulse rate, perfusion index, HbCO, HbMet and other Hb species, and data confidence indicators, such as derived from a pulse oximeter or a Pulse Co-Oximeter™ (Masimo Corporation) to name a few. Invasive parameters may include lactate, glucose or other blood constituent measurements. Capnography parameters may include, for example, end tidal carbon dioxide (ETCO$_2$) and respiration rate. Other measurement parameters that can be input to the parameter processor 101 may include ECG, EEG, blood pressure and temperature to name a few. All of these parameters may indicate real-time measurements or historical data, such as would indicate a measurement trend. Pulse oximetry signal quality and data confidence indicators are described in U.S. Pat. No. 6,684,090 entitled Pulse Oximetry Data Confidence Indicator, assigned to Masimo Corporation, Irvine, Calif. and incorporated by reference herein.

As shown in FIG. 4, monitor outputs 102 may be alarms, wellness indicators, controls and diagnostics. Alarms may be used to alert medical personnel to a potential urgent or emergency medical condition in a patient under their care. Wellness indicators may be used to inform medical personnel as to patient condition stability or instability, such as a less urgent but potentially deteriorating medical state or condition. Controls may be used to affect the operation of a medical treatment device or other medical-related equipment. Diagnostics may be messages or other indicators used to assist medical personnel in diagnosing or treating a patient condition.

User I/O 60, external devices 70 and wireless communication 80 also interface with the parameter processor 101 and provide communications to the outside world. User I/O 60 allows manual data entry and control. For example, a menu-driven operator display may be provided to allow entry of predetermined alarm thresholds. External devices 70 may include PCs and network interfaces to name a few.

Figure 5:
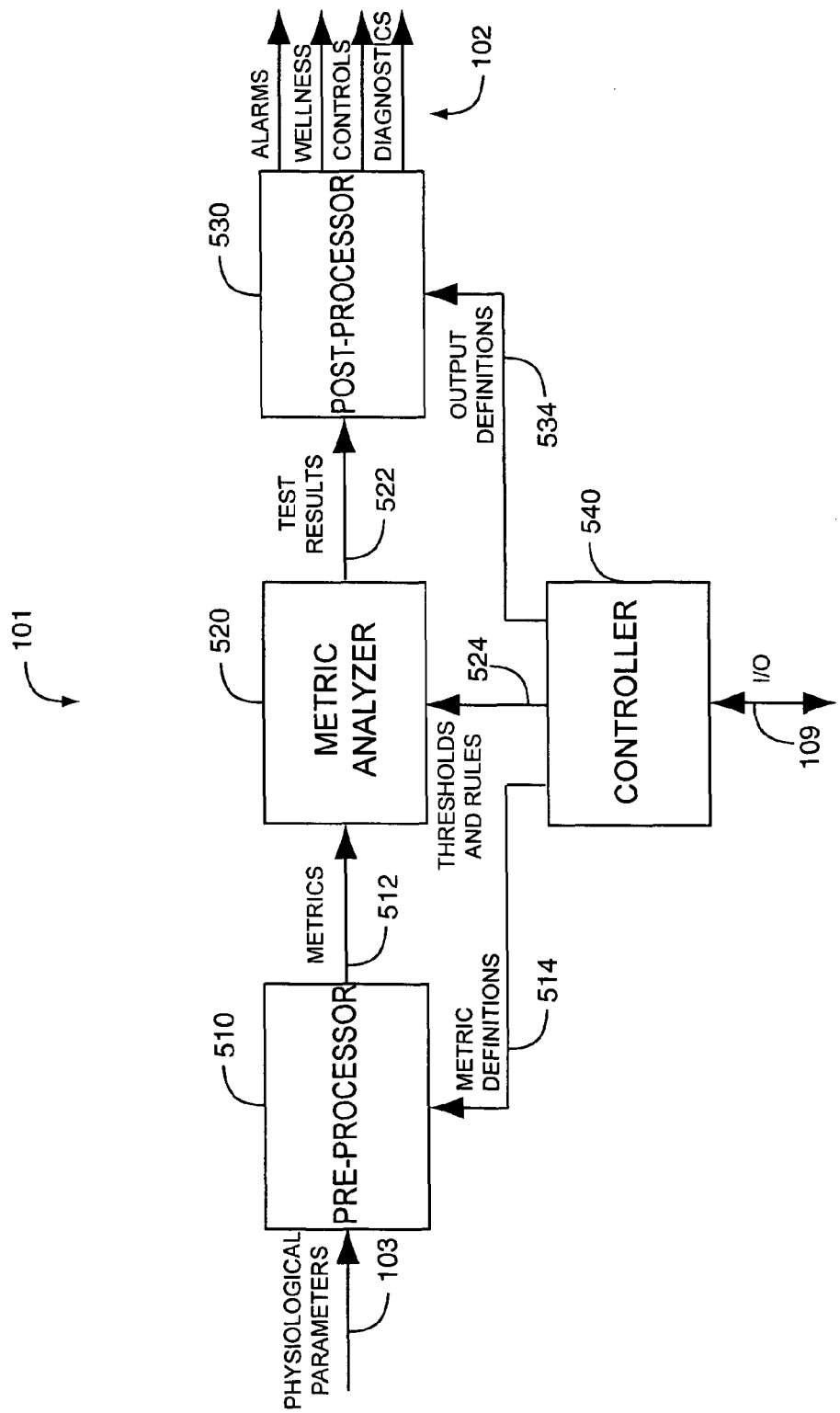
FIG. 5 is a detailed block diagram of a parameter processor embodiment.

FIG. 5 illustrates one embodiment of a parameter processor 101 having a pre-processor 510, a metric analyzer 520, a post-processor 530 and a controller 540. The pre-processor 510 has inputs 103 that may be real-time physiological parameter measurements, historical physiological parameter measurements, signal quality measures or any combination of the above. The pre-processor 510 generates metrics 512 that may include historical or real-time parameter trends, detected parameter patterns, parameter variability measures and signal quality indicators to name a few. As examples, trend metrics may indicate if a physiological parameter is increasing or decreasing at a certain rate over a certain time, pattern metrics may indicate if a parameter oscillates within a particular frequency range or over a particular time period, variability metrics may indicate the extent of parameter stability.

As shown in FIG. 5, the metric analyzer 520 is configured to provide test results 522 to the post-processor based upon various rules applied to the metrics 512 in view of various thresholds 524. As an example, the metric analyzer 520 may output an alarm trigger 522 to the post-processor 530 when a parameter measurement 103 increases faster than a predetermined rate. This may be expressed by a rule that states "if trend metric exceeds trend threshold then trigger alarm."

Also shown in FIG. 5, the post processor 530 inputs test results 522 and generates outputs 102 including alarms, wellness indictors, controls and diagnostics. Alarms may be, for example, audible or visual alerts warning of critical conditions that need immediate attention. Wellness indicators may be audible or visual cues, such as an intermittent, low-volume tone or a red/yellow/green light indicating a patient with a stable or unstable physiological condition. Controls may be electrical or electronic, wired or wireless or mechanical outputs, to name a few, capable of interfacing with and affecting another device. As examples, controls 102 may interface with drug-infusion equipment or medical gas ventilation equipment, as described with respect to FIGS. 2A-C and 3A-C, above.

Further shown in FIG. 5, the controller 540 interfaces with I/O 109, as described with respect to FIG. 4, above. In one embodiment, the I/O 109 provides predetermined thresholds, which the controller 540 transmits to the metric analyzer 520. The controller 540 may also define metrics 514 for the pre-processor 510 and define outputs 534 for the post-processor 530.

A drug administration controller has been disclosed in detail in connection with various embodiments. These embodiments are disclosed by way of examples only and are not to limit the scope of the claims that follow. One of ordinary skill in art will appreciate many variations and modifications.

What is claimed is:

1. A drug administration method comprising:
   receiving, over a period of time, a signal indicative of at least one physiological parameter from a noninvasive optical sensor attached to a patient;
   determining, based on the signal, a plurality of measurements of the at least one physiological parameter, each of the plurality of measurements indicative of a value of the at least one physiological parameter at a different time during the period of time;
   determining, based on the plurality of measurements, at least one parameter trend for the at least one physiological parameter, the at least one parameter trend indicating a rate at which the at least one physiological parameter is increasing or decreasing over the period of time; and
   controlling a drug administration device based at least on one of the at least one parameter trends, wherein the at least one physiological parameter is a measure of blood methemoglobin (HbMet).

2. The drug administration method according to claim 1, further comprising deriving at least one of a parameter limit, a parameter pattern, or a parameter variability.

3. The drug administration method according to claim 1, wherein controlling comprises pausing the drug administration device when HbMet is trending upward.

4. The drug administration method according to claim 1, wherein controlling comprises pausing the drug administration device when HbMet is above a HbMet limit.

5. A drug administration controller comprising:
   at least one noninvasive optical sensor that generates, over a period of time, at least one sensor signal in response to a physiological state of a living being;
   at least one physiological measurement device configured to:
      determine, in response to the at least one sensor signal, a plurality of measurements of at least one physiological parameter, each of the plurality of measurements indicative of a value of the at least one physiological parameter at a different time during the period of time, said at least on physiological parameter including methemoglobin (HbMet); and
      determine, based on the plurality of measurements, at least one trend for the at least one physiological parameter, the at least one trend indicating a rate at which the at least one physiological parameter is increasing or decreasing over the period of time;

a rule-based processor that generates a control output in response to the at least one trend; and a drug administration device responsive to one or more control outputs so as to affect the treatment of the living being including at least one of initiating, pausing, halting or adjusting the dosage of administered drugs.

6. The drug administration controller according to claim 5, wherein the drug administration device is at least one of a drug infusion device or a medical gas inhalation device.

7. The drug administration controller according to claim 5, further comprising a sound sensor attached proximate to a neck site so as to measure respiration rate.

* * * * *